United States Patent [19]

Synnott et al.

[11] 4,105,525

[45] Aug. 8, 1978

[54] INTERNAL STANDARD ELECTROLYTE FOR AMMONIA SENSOR

[75] Inventors: John C. Synnott, Belmont; James W. Ross, Jr., Hull, both of Mass.

[73] Assignee: Orion Research Incorporated, Cambridge, Mass.

[21] Appl. No.: 871,622

[22] Filed: Jan. 23, 1978

[51] Int. Cl.² ............................................ G01N 27/46
[52] U.S. Cl. ................................. 204/195 P; 204/1 T
[58] Field of Search .......... 204/1 T, 1 N, 1 P, 195 R, 204/195 P

[56] References Cited

U.S. PATENT DOCUMENTS

| 3,649,505 | 3/1972 | Strickler et al. | 204/1 N |
| 3,830,709 | 8/1974 | Krueger et al. | 204/195 P |
| 3,830,718 | 8/1974 | Riseman et al. | 204/195 P |
| 3,869,354 | 3/1975 | Montalvo | 204/195 P |

Primary Examiner—T. Tung

[57] ABSTRACT

An ammonia electrode having an internal standard electrolyte solution comprising a saturated aqueous solution of 5,5'-Nitrilodibarbituric acid ammonium salt.

1 Claim, 1 Drawing Figure

U.S. Patent    Aug. 8, 1978    4,105,525
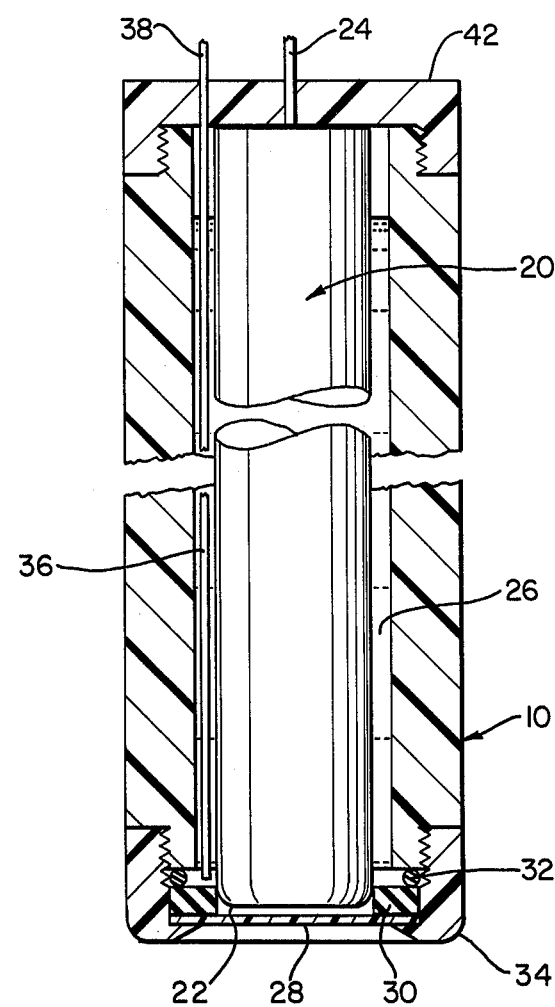

INTERNAL STANDARD ELECTROLYTE FOR AMMONIA SENSOR

BACKGROUND OF THE INVENTION

1. Field of Invention

This invention relates to electrochemical analysis, and particularly to analytical devices in which the ammonia content of sample gases or liquids is measured potentiometrically.

2. Prior Art Statement

Electrochemical methods for the determination of ammonia are typically based on potentiometric measurement of the change in pH caused by diffusion of ammonia into a standard electrolyte solution. Typically, ammonia from a sample liquid or gas enters the electrolyte through a filter or membrane which is selectively permeable to ammonia gas. Ammonia will diffuse into or out of the standard solution until the partial pressure of ammonia is the same on each side of the membrane. Ammonia will react, to some extent, reversibly with water according to the equation:

$$NH_3 + H_2O \rightleftarrows NH_4^+ + OH^-$$

Where $$\frac{[NH_4^+][OH^-]}{[NH_3]} = K$$

K being a constant.

If the standard solution contains a dissolved ammonium salt in sufficient amount, the ammonium ion concentration of the solution may also be considered fixed at K'. Thus, the hydroxyl ion concentration may be considered a function of the ammonia concentration, or $$[OH^-] = [NH_3] K''$$

Where $K'' \alpha K/K'$. The hydroxyl ion concentration is, of course, measurable by a pH electrode or other pH-detecting device, utilizing the relationships:

$$[H^+][OH^-] \simeq 10^{-14}, \text{ and } pH = -\log[H^+].$$

The partial pressure of ammonia, $P_{NH_3}$, in turn, is related to the ammonia concentration by Henry's law:

$$P_{NH_3} = Q[NH_3]$$

Where Q is a proportionality constant dependent on the amount of ammonia or ammonia-producing species in the sample, as well as the sample temperature. In practice, therefore, ammonia concentration is determined by preparing a calibration curve of pH against known ammonia standard solutions which have varying amounts of ammonia spanning the range of expected amounts of the sample. The calibration curves are generated on semilog graph paper by plotting the potential readings, in mv., on the linear axis versus ammonia concentration on the semilog axis, which will give a straight-line calibration curve, in accordance with the Nernst equation.

In the past, the standard electrolyte solution has been typically a dilute solution of a very soluble ammonium salt. For example, in the Strickler et al. U.S. Pat. No. 3,649,505, issued Mar. 14, 1972, a combination pH electrode has a hydrophobic, ammonia-permeable membrane which confines a standard electrolyte consisting of 0.01 M to 3M ammonium chloride adjacent the ion-sensitive glass bulb of the pH electrode. To use the electrode, it is simply dipped into the ammonia-containing sample solution, and the change in potential due to the change in pH is measured when the sample solution and standard electrolyte come to equilibrium.

In practice, a calibration curve is usually first prepared, in which the change in potential resulting from immersing or dipping the electrode into a plurality of different ammonia-containing solutions of known ammonia concentration is measured and plotted on semilog paper against the known concentration. Preparing such curves, then, may require moving the electrode into and out of a series of such known solutions. Acutal measurement of a number of unknown ammonia-containing samples requires moving the electrode into and out of a number of unknown samples, and between sample locations. Unless one is willing to refill the electrode with standard electrolyte solution after each measurement, an obviously inefficient technique, care must be taken that the concentration of the standard electrolyte does not change when the electrode is removed from the ammonia-containing sample solution.

In the Riseman et al. U.S. Pat. No. 3,830,718, issued Aug. 20, 1974, a saturated aqueous solution of an ammonium salt of a strong acid was used as a standard electrolyte to eliminate the possibility of concentration changes due to evaporation of water from the solution. Riseman et al. used ammonium picrate as a preferred internal standard electrolyte. In addition to the benefit that concentration changes by evaporation are eliminated using ammonium picrate as the internal standard electrolyte, Riseman also disclosed a device which may be used to provide accurate determinations of ammonia content of a series of samples without the need for disassembling the electrode and refilling it with standard electrolyte solution.

Federal regulations published by the Materials Transportation Bureau in 49 C.F.R. Sections 170-179 prohibiting the transportation of ammonium picrate on all aircraft, rail cars, and passenger vessels, 49 C.F.R. Section 172.101, with limited exceptions, Section 173.65, make it difficult and expensive to transport ammonium picrate lawfully. Since these regulations took effect in January, 1977, ammonium picrate use as an appropriate internal standard electrolyte has become a practical impossibility.

SUMMARY OF INVENTION

The present invention contemplates a new internal standard electrolyte for use in potentiometric systems to monitor ammonia. The primary object of the invention is to provide an internal standard electrolyte which is not only immune to concentration changes by evaporation, but is also freely transportable under federal regulations.

The object of the invention is effected by providing an electrolyte composed of saturated 5,5'-nitrilodibarbituric acid ammonium salt, also known as ammonium purpurate, acid ammonium purpurate, and "Murexide."

BRIEF DESCRIPTION OF THE DRAWINGS

For a more full understanding of the nature and objects of the present invention, reference should be made to the following detailed description, taken in connection with the accompanying drawing wherein there is shown a diagrammatic cross-sectional view of an electrode containing the electrolyte solution of the invention.

DETAILED DESCRIPTION OF THE INVENTION

Referring now to the drawing, there will be seen a specific embodiment of an ion sensitive electrode embodying the principles of the present invention and comprising a substantially tubular body or barrel 10 of electrically nonconductive, substantially chemically inert material such as polytetrafluorethylene or the like. Disposed within the hollow interior of tube 10 is a first electrode, indicated generally at 20. Electrode 20 is any of a number of well known pH glass electrodes which are usually formed as a hollow cylinder of a non-conducting glass, closed at one end by a bulb or membrane 22 of a hydrogen-ion sensitive glass. Such pH electrodes also include an internal reference electrode, typically Ag/AgCl (not shown), immersed in a suitable electrolyte filling solution. The internal reference element of the pH electrode is connected to external lead 24.

Barrel 10 is internally dimensioned so that there is a substantial interspace between the external periphery of pH electrode 20 and the inside of barrel 10. Disposed within that interspace is internal solution 26.

Membrane 22 of pH electrode 20 is supported about its periphery by one side of spacer ring 30. Stretched across the other side of spacer ring 30 and thereby held at a precisely predetermined distance from membrane 22, is membrane 28. Spacer ring 30 is sealed to an end of barrel 10 by elastomeric O-ring 32. Spacer ring 30, O-ring 32 and membrane 28 are all releasably held in a predetermined position with respect to membrane 22 by cap 34 which is threadedly mounted on barrel 10. A second or reference electrode 36, typically an Ag/AgCl wire, is also disposed in contact with solution 26 to complete an electrochemical cell. Electrode 36 is coupled to external lead 38. The other end of barrel 10 is preferably closed by cap 42 which also serves as a support for leads 24 and 38.

Membrane 28 is preferably held by cap 34 and spacer ring 30 so that the interspace between the pH sensitive membrane 22 and the ammonia-permeable membrane 28 is very thin. Thus, because the interspace communicates with the body of solution 26, it will contain a very thin film, typically a few mil, of solution 26.

Membrane 28 is formed of a microporous hydrophobic material having a porosity sufficiently great so as to readily pass ammonia gas but not great enough to permit any appreciable passage of liquid or ions. Preferably membrane 28 comprises a thin (from 0.005 to 0.007 inch thick) disc of microporous polytetrafluoroethylene having an average pore size of about 0.6 microns and an average free area in the range of about 50%.

Suitable membrane materials are set forth in the aforesaid Strickler patent, and include polyvinylidene fluoride (specifically, Gelman's "Metricel VF-6") and polyvinyl chloride, as well as hydrophilic membranes treated with a water repellent such as dimethyl dichlorosilane, and perfluorinated cationic surfactants (e.g., DuPont "Zepel" and 3 M's "FC805").

The standard electrolyte solution is a saturated solution ($6 \times 10^{-3}$M at room temperature) of 5,5'-Nitrilodibarbituric acid ammonium salt, also known as ammonium purpurate and acid ammonium purpurate, (available as "Murexide" from Fisher Scientific Co., Fair Lawn, New Jersey, 07410). To provide a standard chloride concentration for the reference Ag-AgCl electrode, the electrolyte also contains a known amount of a dissolved chloride salt such as NaCl, KCl or the like, preferably about $10^{-4}$ to $10^{-1}$ moles/liter of ammonium chloride or sodium chloride.

One illustrative method of use of this electrode will now be described. With the electrode connected to a suitable high input impedance potentiometric device (e.g., a standard pH meter), a calibration curve is prepared by inserting the electrode into a series of ammonia standardizing solutions of successively increased known ammonia concentrations and the potential across leads 24 and 38, read out in millivolts, is recorded and plotted in semilog graph paper. The standardizing solutions are chosen to bracket the expected ammonia concentration of the sample by at least an order of magnitude on each side of the expected concentration, e.g., $10^{-4}$, $10^{-3}$, $10^{-2}$, etc. M ammonium chloride. The mv. readings are plotted on semilog graph paper in the linear axis against concentration on the semilog axis.

The sample solution is then prepared. This solution must, because of the partial pressure relationship previously discussed, be at substantially the same temperature and have substantially the same composition of dissolved species as the standardizing solution. In practice, this is carried out for samples containing low levels of dissolved species by adding sodium hydroxide (typically, 1 ml. of 10 M NaOH per 100 ml. of sample). Samples having high levels of dissolved species should first be diluted, and then sodium hydroxide added as before.

Finally, the electrode is dipped into the sample solution, and the pH read out in millivots. This pH can then be converted to ammonium concentration by use of the calibration curve.

Other embodiments will occur to those skilled in the art and are within the following claims.

What is claimed is:

1. In an electrochemical cell for measuring the ammonia content of a sample, said cell including a potentiometric hydrogen ion-sensitive electrode and a reference electrode both in contact with an internal standard electrolyte, said cell having an ammonia-permeable filter arranged to separate the sample from the electrodes and the electrolyte such that ammonia from the sample can pass through the filter into the electrolyte to affect the hydrogen ion activity of the electrolyte, the improvement wherein the internal standard electrolyte comprises a saturated aqueous solution of 5,5'-Nitrilodibarbituric acid ammonium salt.

* * * * *